(12) United States Patent
Redon

(10) Patent No.: US 7,185,655 B1
(45) Date of Patent: Mar. 6, 2007

(54) UNDERWATER EAR PROPHYLACTIC

(76) Inventor: John Robert Redon, 3329 Parade Pl., Lake Worth, FL (US) 33462

( * ) Notice: Subject to any disclaimer, the term of this patent is extended or adjusted under 35 U.S.C. 154(b) by 0 days.

(21) Appl. No.: 10/884,577

(22) Filed: Jul. 3, 2004

(51) Int. Cl.
*A61F 11/00* (2006.01)

(52) U.S. Cl. .................. 128/864; 181/129; 128/867; 128/868

(58) Field of Classification Search .......... 128/864, 128/865, 867, 868; 181/129, 130, 128, 134, 181/135

See application file for complete search history.

(56) References Cited

U.S. PATENT DOCUMENTS

| | | | |
|---|---|---|---|
| 2,437,490 A | | 3/1948 | Watson |
| 5,488,961 A | | 2/1996 | Adams |
| 5,865,183 A | * | 2/1999 | Hirschebain ............... 128/864 |
| 5,881,729 A | | 3/1999 | Castillo |

* cited by examiner

*Primary Examiner*—Patricia Bianco
*Assistant Examiner*—Camtu Nguyen
(74) *Attorney, Agent, or Firm*—Dorothy S. Morse

(57) ABSTRACT

The present invention provides a prophylactic for the ear during activities in and around water or other liquid medium where the ear is subject to infection and barotraumas. It has an outer ear section that fits tight in a user's outer ear and a watertight downwardly extending flexible protrusion that extends into the outer part of the ear canal. A non-collapsing, flexible sleeve with a hollow interior is concentrically positioned within the outer ear section and flexible protrusion. A diaphragm with elastic and water-resistant properties is attached across one end of the sleeve with watertight sealing means. An optional protuberance and/or lanyard may be attached to the outer ear section to assist in prompt invention removal after use, and an external barrier is optional where sudden impact can occur. For water depths below thirty-three feet, the diaphragm should be positioned near or within the flexible protrusion portion of the device.

20 Claims, 2 Drawing Sheets

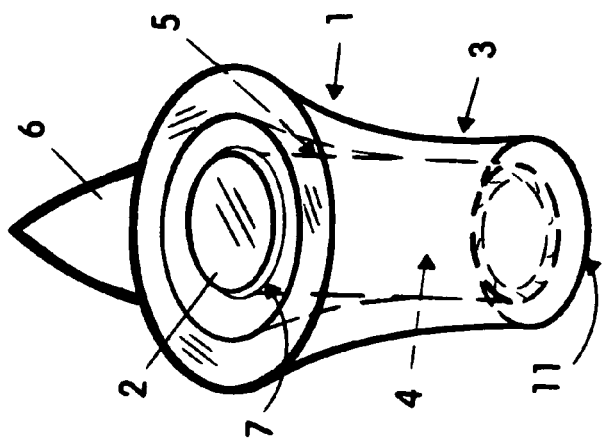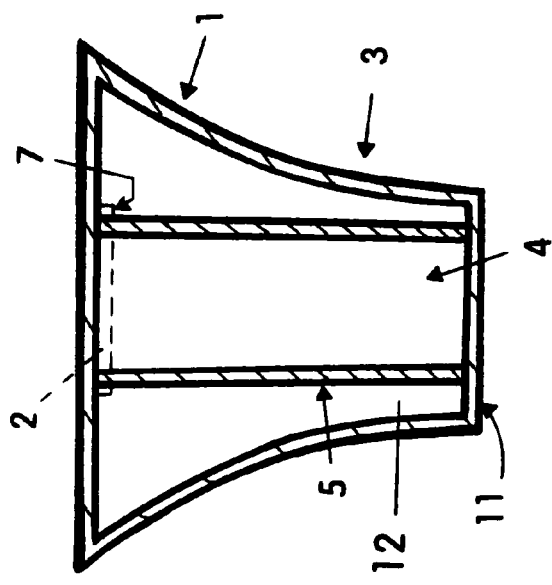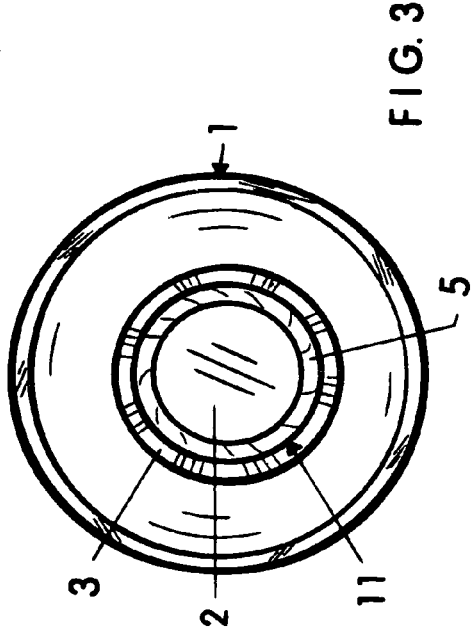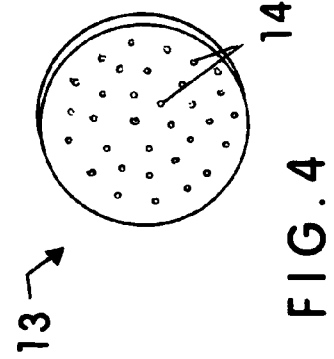

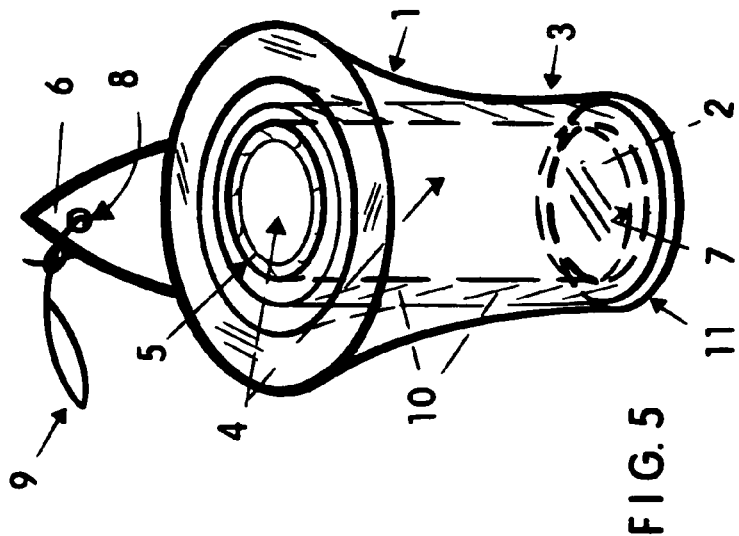
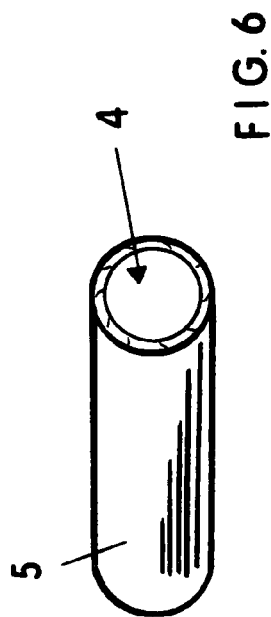
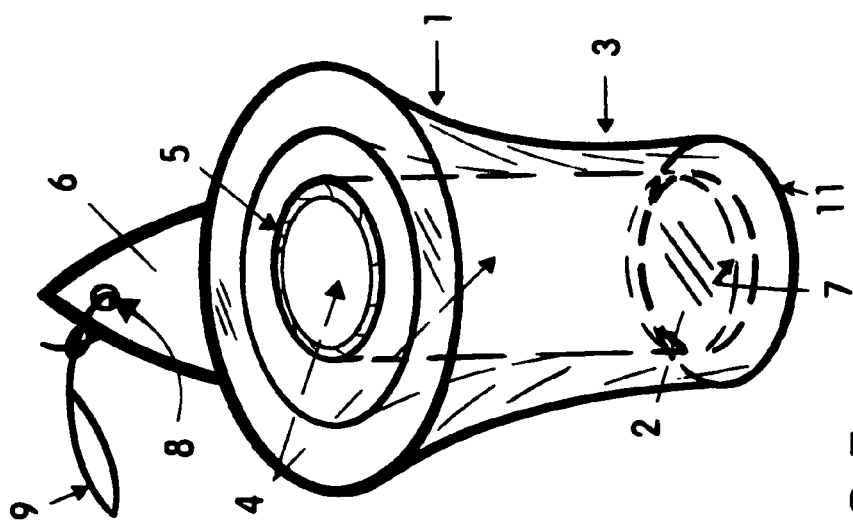

UNDERWATER EAR PROPHYLACTIC

CROSS-REFERENCE TO RELATED APPLICATIONS

None

BACKGROUND OF THE INVENTION

1. Field of the Invention

This invention relates to prophylactics for the ear that keep harmful foreign objects from contacting the ear canal and ear drum of a user when he or she is positioned at or below the surface of fresh water, saltwater, or any other liquid medium that is likely transport unwanted foreign matter into an ear. The present invention, which may be reusable, provides protection of a user's ear from barotraumas and infection when the user is subjected to pressures ranging from one to approximately twelve atmospheres. This makes the present invention ideal for use by those engaging in surface and subsurface marine construction and maintenance, as well as use by sport divers. Unless the diaphragm is protected by an optional external barrier, it is not contemplated for the present invention to be used in activities where a sudden impact might occur to the ear, such as but not limited to water skiing, use of personal watercraft, snow skiing, use of snow mobiles, and surfing.

2. Description of the Related Art

Commercial divers, pile drivers, hull scrapers, and others often work in shallow water without any type of ear protection against water or fluid carried infection-causing contaminants, even though their work environment repeatedly places their ear drums and ear canals at risk for exposure to unhealthy substances, such as mud, barnacles, oil, hydraulic fluid, creosote, organic materials, plant and animal life, bacteria, and other debris. Sport divers also place themselves at risk for ear disorders every time they dive and snorkel without ear protection in water that contains infection causing debris and bacteria, an occurrence that appears to be of increasing concern in recreational waters. Although many types of ear plugs exist, until use of the present invention, none appear to completely block the passage between the outer ear and the ear drum while concurrently allowing the equalization of pressure through the use of an elastic diaphragm positioned across one end of an inner sleeve. Preferably, the diaphragm end of the inner sleeve is positioned remote from the outer ear, however, when using the present invention where pressures would not exceed approximately two atmospheres, it is considered to be within the scope of the present invention for the diaphragm end of the sleeve to be in a reversed position remote from the ear canal. When the elastic diaphragm is positioned closer to the ear canal, the displacement needed to equalize pressure is less than when the present invention diaphragm is positioned remotely from the ear canal. Optionally, an additional seal can be used between the present invention body and sleeve to help the body fit more snugly within the user's outer ear, such as but not limited to a non-drying permanently tacky glue. No ear prophylactic is known that has the same structure or all of the advantages offered by the present invention.

The invention is thought to be most closely associated with the present invention is U.S. Pat. No. 5,488,961 to Adams (1996). However, there are important differences between the Adams invention and the present invention. Adams discloses a hollow elongated earplug with a uniformly tapering outer surface and a lumen along the ear canal. A hydrophobic membrane extends across the lumen to selectively block water entry into the ear canal while admitting air movement into and out of the ear canal to equalize air pressure and improve the user's hearing. The Adams membrane extends laterally into the interior walls of the plug body. Optionally, for ear protection when greater fluid pressures are involved, the Adams membrane can have a support structure, which is shown and described to be two concentric circles joined by four radial extensions. The support structure is always on the side of the membrane adjacent to the distal end of the plug body. When such a support structure is used, it also extends laterally into the interior walls of the plug body. A third optional Adams structure is disclosed, which allows for substitution of membranes having different pore diameters, water break through ratings, and/or air flow rates for use at different fluid depths. The Adams membrane and its support structure are then secured laterally within the interior surface of a mounting assembly that is removable from the plug body. Although the Adams mounting assembly is generally cylindrical, it has a step-down configuration that gives its distal portion 36B a smaller diameter than its proximal portion 36A. Thus, when the Adams plug body is removed from an ear, a new mounting assembly with a different membrane can be inserted into the plug body in place of the previously used mounting assembly/membrane combination. The present invention can be distinguished from the Adams invention in several important ways. First, the present invention diaphragm is different from the Adams membrane. While the Adams membrane selectively allows air to pass through it, but not water and debris, the present invention stretchable diaphragm completely blocks entry of everything from getting into the ear canal, including air. Thus, the Adams membrane equalizes pressure by letting air pass through it, while the present invention stretchable diaphragm equalizes pressure by physical displacement. Also, the present invention device is simpler in construction and discloses a different exterior plug configuration than the Adams invention. While the exterior configuration of the Adams invention is uniformly tapering, the corresponding feature of the present invention has a two-stage tapering configuration with the difference in the diameter of wide end to narrow end being greater for the outer ear section instead of the opposing ear canal section. Further, the membrane of the present invention is sealed across one end of a non-collapsing, flexible, and hollow cylindrical sleeve, while the membrane of the Adams invention extends laterally into the walls of the plug body or a mounting assembly positioned within the plug body. When the Adams invention uses a mounting assembly, its plug body must have an interior surface with a step-down configuration at one end to accommodate the complementary exterior step-down configuration on the exterior surface of the Adams mounting assembly. The step-down configuration would prevent reverse end-to-end orientation of the Adams mounting assembly, whereby the sleeve of the present invention has no step-down exterior configuration so that its end-to-end orientation can be reversed when preferred for use in fluids with differing pressures. The need for the Adams membrane support structure to always remain adjacent to the distal end of the plug body would also prevent the end-to-end reversal of the Adams mounting assembly. Also, the Adams invention teaches replacement of its mounting assembly with another having a new membrane configured for use at a different fluid depth, while the present invention discloses reversing the end-to-end orientation of its sleeve for fluid pressure adaptation by a single membrane between one and approximately twelve atmospheres. Thus, the Adams invention does not teach all of the structure and advantages provided by the present invention.

Other earplug inventions having pressure equalizing membranes or partitions are U.S. Pat. No. 5,881,729 to Castillo (1999) and U.S. Pat. No. 2,437,490 to Watson (1948). Watson discloses a hollow and elongated pressure-regulating earplug that equalizes pressure in the user's ear canal and also provides sound insulation. The Watson invention has a flared outer portion, an opposing orifice, and a reduced inner portion between the outer portion and the orifice with the inner portion having spaced flanges on its exterior surface and a substantially cylindrical configuration. Watson further has one or two partitions between the flared outer portion and the orifice, with each partition having an air pressure equalizing unit that is acoustically packed with cotton or other packing material that muffles sound yet permits the rapid equalization of air pressure in the ear canal through the plug. The Watson invention does not teach a removable rigid inner sleeve with a stretchable diaphragm on one of its ends that equalizes pressure by physical displacement. In contrast, Castillo discloses a hollow elongated water sports earplug that has a membrane to prevent wind and water from entering a user's ear while permitting sound to pass through the membrane. The exterior configuration of the Castillo invention plug body is similar to that of the Watson invention, with a flared outer portion, an opposing orifice, and a reduced inner portion between the outer portion and the orifice, with the inner portion having a substantially cylindrical configuration. However, instead of partitions with air pressure equalizing units that are acoustically packed with sound blocking material, the Castillo invention has an insert that fits into its cylindrical inner portion. The insert has an annular retaining member, a membrane, and a generally annular insert housing for the membrane which positions the membrane axially close the second end of the insert housing. Thus, when the insert is located within the plug body, it does not extend the full length of the plug body, leaving the membrane positioned between the flared outer portion and the reduced inner portion of the Castillo invention. In contrast, the non-collapsing, flexible present invention inner sleeve extends the full length of its respective plug body. Also, its diaphragm is preferably positioned at the orifice end of its respective plug body, although it is also possible to position the present invention diaphragm remote from the ear canal. However, in either of its two possible positions, since the inner sleeve of the present invention is substantially similar in length to its respective plug body and its stretchable diaphragm is positioned across one of the opposing ends of the sleeve, the diaphragm of the present invention does not have a centered positioning within its plug body, as is taught by the Castillo invention.

BRIEF SUMMARY OF INVENTION—OBJECTS AND ADVANTAGES

It is the primary object of this invention to provide an ear protection device that completely blocks the ear canal and prevents anything from getting into it, including but not limited to harmful foreign objects, water, air, and other gases. A further object of the present invention is to provide an ear protection device that permits pressure equalization in the ear canal to prevent barotraumas when the user is positioned at or below the surface of fresh water, saltwater, or other liquid medium. It is also an object of the present invention to provide an ear protection device that fits securely and comfortably within a user's outer ear for extended use. A further object of the present invention is to provide an ear protection device that is quick and easy to install and remove from a human ear. It is a further object of the present invention to provide an ear protection device against infection and barotraumas that can be reusable.

The present invention has an outer ear section that fits water tight in the user's outer ear with a watertight flexible protrusion extending therefrom into the outer portion of the user's ear canal. Although not limited thereto, silicon is one preferred material contemplated for manufacture of the outer ear section and watertight flexible protrusion. If needed, a non-drying permanently tacky glue, or similar fastening substance, can be used to improve the watertight seal between the outer ear section and the user's outer ear. Once the outer ear section is in place, a flexible but non-collapsing sleeve with a hollow interior is concentrically positioned within the outer ear section so that a connected diaphragm becomes located between the user's outer ear and his or her ear canal. Non-drying permanently tacky glue or resilient inner sleeve can be used between the outer ear section and the non-collapsing flexible sleeve to improve the required watertight/airtight seal. Optionally, a porous external barrier may be secured over the outer ear section to prevent large objects, such as but not limited to barnacles, from becoming lodged in the diaphragm. Such a barrier would also protect the present invention diaphragm from harm during activities such as but not limited to water skiing, use of personal watercraft, snow skiing, use of snow mobiles, and surfing, where a sudden impact to the ear is likely to occur. The sleeve typically has round or oval cross-sectional configuration, but is not limited thereto, and extends substantially the full length of the outer ear section. In addition, the diaphragm has elastic properties and is positioned across one end of the sleeve to provide a watertight and airtight seal to block all substances from entering the user's ear canal through the hollow interior of the non-collapsing flexible sleeve. When the present invention is used in and around water depths from zero feet to approximately minus thirty-three feet, or up to pressures of approximately two atmospheres, although preferred in an opposed position, the sleeve can be placed with within the outer ear section so that the diaphragm is remote to the ear canal. However, in its preferred position, and particularly when the present invention is used at water depths at or below minus thirty-three feet, or at pressures approximating or greater than two atmospheres, the sleeve is placed within the outer ear section so that the elastic diaphragm is adjacent to the user's ear canal. Physical displacement of the membrane as a result of stretching toward a user's ear canal provides that pressure equalization for the ear that prevents barotraumas. This occurs due to the present invention defining a dead air space in the ear canal between the eardrum and the diaphragm. As the user of the present invention moves to a greater depth in the water or other liquid medium and the exterior pressure increases, the volume of the dead air space decreases in the ear canal between the ear drum and the diaphragm causing the diaphragm to dilate into the dead air space for pressure equalization without barotraumas to the ear drum. When the diaphragm in positioned remote from the user's outer ear, less physical displacement of the diaphragm occurs than when it is adjacent to the outer ear. Also, since the greatest diaphragm stretching occurs in water depths up to thirty-three feet, and the greatest displacement then occurring is approximately one-fourth of an inch, it is contemplated for present invention use to be possible to water pressures approximating twelve atmospheres that would be experienced at water depths of approximately four hundred feet. A further option for the present invention is to have a lanyard bonded to the exterior portion of the outer ear section to assist in prompt and easy removal of the entire present invention assembly from a user's ear.

BRIEF DESCRIPTION OF THE SEVERAL VIEWS OF THE DRAWINGS

FIG. 1 is a side sectional view of a first preferred embodiment of the present invention ear protection device having an outer ear section with a large end, a tapered smaller end, and a flexible protrusion downwardly depending from the tapered smaller end, a non-collapsing, flexible sleeve with a hollow interior concentrically positioned within the outer ear section and the flexible protrusion, the sleeve extending substantially through the full length of the combined outer ear section and flexible protrusion, the non-collapsing sleeve also having a diameter dimension close to that of the flexible protrusion, and a diaphragm being attached with a sealing means across the end of the sleeve positioned within the outer portion's large end.

FIG. 2 is a perspective view of a second preferred embodiment of the present invention ear protection device having an outer ear section with a large end, a tapered smaller end, and a flexible protrusion downwardly depending from the tapered smaller end, a protuberance or tab upwardly extending from the upper edge of the outer ear section, a non-collapsing, flexible, and hollow sleeve concentrically positioned within the outer ear section and the flexible protrusion, the non-collapsing sleeve extending substantially through the full length of the combined outer ear section and flexible protrusion, the sleeve also having a similar diameter dimension to that of the flexible protrusion, and a diaphragm being attached with a sealing means across the end of the sleeve adjacent to the protuberance.

FIG. 3 is a top view of the first preferred embodiment of the present invention ear protection device with the non-collapsing sleeve concentrically positioned within the outer ear section, a portion of the inside surface of the flexible protrusion being visible adjacent to the sleeve, and a diaphragm secured across the end of the sleeve positioned within the flexible protrusion.

FIG. 4 is a top perspective view of a preferred embodiment for a porous barrier used as an optional part of the present invention ear protection device to keep large objects from impacting the diaphragm.

FIG. 5 is a perspective view of a third preferred embodiment of the present invention ear protection device having a non-collapsing sleeve positioned within the outer ear section and the flexible protrusion downwardly depending therefrom, and further having a sealing means between the sleeve and the outer ear section.

FIG. 6 is a perspective view of a preferred embodiment of the present invention non-collapsing sleeve having a substantially cylindrical configuration.

FIG. 7 is a perspective side view of the third preferred embodiment of the present invention ear protection device having an outer ear section with a large end, a tapered smaller end, and a flexible protrusion downwardly depending from the tapered smaller end, a protuberance or tab upwardly extending from the upper edge of the outer ear section, the protuberance having an aperture therethrough and a lanyard secured through the aperture, a non-collapsing, flexible sleeve with a hollow interior concentrically positioned within the outer ear section and the flexible protrusion, the non-collapsing sleeve extending substantially through the full length of the combined outer ear section and flexible protrusion, the sleeve also having a diameter dimension close to that of the flexible protrusion, and a diaphragm being attached with a sealing means across the end of the sleeve positioned within the flexible protrusion.

DETAILED DESCRIPTION OF THE INVENTION

Many features of the present invention will become clear upon reference to the included drawings. However, the drawings are included for the purpose of providing an illustration of preferred embodiments for the present invention, and it is not intended for them to be limiting. Thus, the appended claims and their legal equivalents should be used to determine the scope of the improved present invention, rather than the scope being limited to the examples given below and/or other places in the specification and drawings.

The present invention is a prophylactic for protecting a human ear (not shown) from infection and barotraumas while its user is positioned at or below the surface of water or another liquid medium where the pressure to which the ear is subjected ranges between approximately one and twelve atmospheres. FIG. 1 shows the present invention having an outer ear section 1 with a large end and a smaller tapered end, the tapering configuration being configured to fit tight but comfortably into a user's outer ear (not shown). Although not shown, if for any reason the fit of the outer ear section is not water tight or perceptively secure in the user's outer ear, a non-drying permanently tacky glue or other similar functioning substance can be used to hold the present invention in position. A flexible protrusion 3 downwardly depends from the smaller tapered end of outer ear section 1. Protrusion 3 has a more gradual tapering configuration than outer ear section 1. It is intended for protrusion 3 to have a sufficient length dimension for its bottom end 11 to extend into the user's outer ear canal (not shown). Although not limited thereto, it is contemplated for outer ear section 1 and flexible protrusion 3 to be joined together by unitary construction. Preferably also, but not limited thereto, it is contemplated for the combination of outer ear section 1 and flexible protrusion 3 to be made at least in part from closed cell neoprene or silicone materials. FIG. 1 further shows a non-collapsing, flexible sleeve 5 with a hollow interior 4 being concentrically positioned within outer ear section 1 and protrusion 3, and extending through the full length of both. The space 12 shown in FIG. 1 between sleeve 5 and flexible protrusion 3 is somewhat exaggerated for illustrative purposes, since once the present invention ear prophylactic device is positioned within an ear, it is contemplated for the outside surface of at least the lower end of sleeve 5 to be in airtight/watertight contact with the opposing inside surface of flexible protrusion 3, so as to fit snugly within flexible protrusion 3 without additional sealant, although where needed it is contemplated for a sealing means to be used, such as that shown by the number 10 in FIG. 5. However, prior to insertion of the present invention within an ear, the diameter of sleeve 5 should be slightly smaller than that of flexible protrusion 3, so that sleeve 5 can be easily and promptly placed into its usable position within flexible protrusion 3. Once sleeve 5 and flexible protrusion are placed within a user's ear, the airtight/watertight seal will not only be achieved between flexible protrusion 3 and sleeve 5, but between flexible protrusion 3 and adjacent outer ear canal tissue as well. Thus, the space 12 shown in FIG. 1 between sleeve 5 and flexible protrusion 3 would always be eliminated immediately prior to use, either as a result of the flexible material of protrusion 3 being forced against sleeve 5 by the adjacent tissues in the user's outer ear canal, or by use of a resilient sealing sleeve or tube 10, or other sealing means, that would surround sleeve 5 and fill in and/or otherwise eliminate space 12, as shown in FIG. 5. Although FIG. 1 shows sleeve 5 being substantially the same length dimension as the combined outer ear section 1 and flexible protrusion 3, and aligned therewith so as not to extend beyond outer ear section 1 or flexible protrusion 3, during actual use it is considered to be within the scope of the present invention for sleeve 5 to extend in part beyond bottom end 11. FIG. 1 further shows a diaphragm 2 made of elastic and water/air resistant materials being attached to the end of sleeve 5 that is positioned within outer ear section 1. Watertight/airtight sealing means 7 secures diaphragm 2 to sleeve 5. Between water depths of zero to thirty-three feet, where fluid pressures are typically less than two atmospheres, diaphragm 2 can be positioned within outer ear section 1, as shown in FIG. 1, or within flexible protrusion 3. Less displacement of diaphragm 2 occurs when it is placed closer to the user's ear canal. For water depths below thirty-three feet and where fluid pressures are greater than two atmospheres, diaphragm 2 must be positioned within flexible protrusion 3, as shown in FIGS. 4 and 5. Although FIG. 1 shows sleeve 5 having a round cross-sectional configuration, it is not limited thereto.

FIG. 2 shows a second preferred embodiment of the present invention substantially similar to the first embodiment shown in FIG. 1, wherein sleeve 5 has a hollow interior 4 and is concentrically positioned within outer ear section 1, and sleeve 5 fully extending through outer ear section 1 and flexible protrusion 3. However, in FIG. 2 the wall thickness of outer ear section and flexible protrusion 3 appears to be greater than shown for the first preferred embodiment in FIGS. 1 and 3. In addition, the second preferred embodiment has a substantially triangular-shaped protuberance 6 extending upwardly beyond the top perimeter of from outer ear section 1, which has sufficient dimension and configuration to assist a user in prompt and easy removal of the entire present invention from an ear when its use is not longer needed. FIG. 2 shows diaphragm 2 in the same orientation used in FIG. 1, where it is attached with a watertight seal 7 to the end of sleeve 5 positioned within the larger outer ear end of outer ear section 1. Watertight seal 7 can include any type of non-toxic sealing or bonding agent that does not weaken the material in diaphragm 2 or affect its ability to stretch, but is not limited to adhesives and bonding agents per se. In addition, although FIG. 2 shows protuberance 6 having a substantially triangular-shaped extending upwardly beyond the top perimeter of outer ear section 1, its size and shape are not critical, and it is contemplated for protuberance 6 to have any dimension and configuration that facilitates prompt and easy user removal of the present invention from an ear. However, to reduce manufacturing cost and enhance performance, it is contemplated for protuberance 6 and outer ear section 1 to be joined together by unitary construction and made from the same material or materials used for outer ear section 1 and its downwardly depending protrusion 3.

FIG. 3 shows the first preferred embodiment of the present invention ear protection device with its non-collapsing sleeve 5 concentrically positioned within outer ear section 1 and the flexible protrusion 3 downwardly depending from outer ear section 1. However, FIG. 3 is different from FIG. 1 in that the bottom portion of sleeve 5 is in close contact with the bottom end 11 of flexible protrusion 3, with no space 12 being present therebetween. FIG. 3 also shows diaphragm 2 being attached to the end of non-collapsing sleeve 5 positioned within the flexible protrusion 3, a position that is reversed from that shown in FIG. 1. FIG. 4 shows one preferred embodiment of a porous barrier 13 that can be used as an optional part of the present invention ear protection device to keep large objects (not shown), such as but not limited to barnacles, from impacting diaphragm 2. Use of barrier 13 can also protect diaphragm 2 from harm due to sudden impact to the ear that is likely to occur during activities such as but not limited to water skiing, use of personal watercraft, snow skiing, use of snow mobiles, and surfing. Although for most uses it is contemplated for the preferred barrier 13 to have a small thickness dimension, its perimeter dimensions are not critical as long as it can be sealed to outer ear section 1 in a protective position over sleeve 5 and its attached diaphragm 2. The sealing means used to attach barrier 13 to outer ear section 1 may vary, and include the non-drying permanently tacky glue used to secure outer ear section to outer ear tissue or other sealing means, including but not limited to other non-toxic adhesives and/or bonding agents. Also, it is not critical to have pores 14 that are a visible part of the surface structure of barrier 13, and pores 14 do not have to be round. Further, in the alternative, barrier 13 may be made from materials having a mesh or screen-like configuration. It is not contemplated for barrier 13 to be stretchable, and it may be made from flexible or rigid materials.

FIGS. 5 and 7 show a third preferred embodiment of the present invention ear protection device wherein a protuberance or tab 6 is upwardly extending from one portion of the upper edge of outer ear section 1, with the protuberance/tab 6 having an aperture 8 therethrough and a lanyard 9 secured through aperture 8. The size and configuration of aperture 8 and lanyard 9 are not critical as long as each permits lanyard 9 to be used in combination with protuberance/tab 6 for prompt extraction of the present invention ear prophylactic device from an ear. FIGS. 5 and 7 both show outer ear section 1 having a large end, a tapered smaller end, and a flexible protrusion downwardly depending from its tapered smaller end. Non-collapsing, flexible sleeve 5 with its hollow interior 4 is concentrically positioned within outer ear section 1 and flexible protrusion 3. Further, FIGS. 5 and 7 shows sleeve 5 extending substantially through the full length of the combined outer ear section 1 and flexible protrusion 3. Although sleeve 5 does not have to have an identical length dimension to that of the combined outer ear section 1 and flexible protrusion 3, it is contemplated that due to the relatively small size of the present invention device needed to fit within a human ear, that sleeve 5 would extend substantially the fully dimension between the top of outer ear section 1 and bottom end 11. FIGS. 5 and 7 further show diaphragm 2 being attached with sealing means 7 across the end of sleeve 5 positioned within flexible protrusion 3, and sleeve 5 having a diameter dimension close to that of the flexible protrusion 3, with the space 12 shows between similar components in FIG. 1 being eliminated. Sealing means 7 may comprise and physical or chemical substance, or combination thereof, which allows diaphragm 2 to stretch without restriction to protect a user's ear from barotraumas. The visible and most significant difference between FIGS. 5 and 7 are that FIG. 5 shows a sealing means 10 secured tightly between sleeve 5 and flexible protrusion 3. It is contemplated for sealing means 10 to have a resilient sleeve-like or tube-like structure, as shown in FIG. 5, or be a resilient but amorphous non-toxic substance that surrounds sleeve 5 and fills the space 12 (not shown in FIG. 5) between sleeve 5 and flexible protrusion 3. FIG. 6 shows the preferred embodiment of the present invention non-collapsing, flexible sleeve 5 having a substantially cylindrical configuration and a hollow interior 4. However, it is not contemplated for the configuration of sleeve 5 be limited to that of a circular cross-section, as an oval or other curved or curvilinear perimeter configuration may also be appropriate for specific applications. Also, the hollow interior 4 of sleeve 5 may have a different configuration than that for the outside surface of sleeve 5, and the wall thickness of sleeve 5 relative to its inside dimension may vary from that shown in FIG. 6. However, it is contemplated for the inside and outside wall thickness dimensions at one end of sleeve 5 to extend along its entire length. Although not limited thereto, it is contemplated in the most preferred embodiments of the present invention ear prophylactic device for diaphragm 2 to be made from rubber, latex, or closed cell neoprene materials, and for outer ear section 1 and flexible protrusion 3 to be made from silicone or wax materials. Further, although not limited thereto, it is contemplated in the most preferred embodiments of the present invention ear prophylactic device for sleeve 5 to be made from a polypropylene material. In addition, sleeve 5, outer ear section 1, and flexible protrusion 3 can all be made from the same material or materials, or different materials, including outer ear section 1 being made from a less dense material that is better able to conform to a user's outer ear. Although it is contemplated for sleeve 5 and its attached diaphragm 2 to be primarily used with outer ear section 1 and flexible protrusion 3, it is also considered to be within the scope of the present invention for sleeve 5 and its attached diaphragm 2 to be retrofitted to other ear protection devices having an outer ear canal component, with additional sealing means if required to achieve an airtight/watertight seal between the outside surface of sleeve 5 and the inside surface of the outer ear canal component into which it is positioned during use. If the interior end of the outer ear canal component is solid in construction, a hole will have to be formed through the interior end to allow for the displacement of diaphragm 5 needed for pressure equalization.

What is claimed is:

1. An ear prophylactic device for the ears of users operating at or below the surface of water and other liquid media, at depths less than thirty-three feet as well as depths greater than thirty-three feet, to prevent an ear from being adversely affected by infection and barotraumas, said device comprising:
   a tapering and centrally void outer ear member configured and dimensioned for a watertight and airtight fit within a user's ear, said outer ear member having a wide end and a narrow end, said outer ear member also having a centrally void flexible protrusion depending from said narrow end and extending into the user's ear canal;
   a non-collapsing, flexible sleeve having a hollow interior and opposite ends, said sleeve being configured and dimensioned for concentric positioning within said flexible protrusion;
   a stretchable diaphragm made from water-resistant and air-resistant material; and
   sealing means adapted for sealing said diaphragm across one of said opposite ends of said sleeve so that when a user of said device is intending to enter a liquid medium greater than thirty-three feet in depth said sleeve is positioned within said flexible protrusion in a manner that places said diaphragm adjacent to said flexible protrusion to allow stretching diaphragm movement toward the user's ear canal to provide pressure equalization in response to changes in liquid pressure, and when a user intends to remain at liquid depths less than thirty-three feet said sleeve is positioned within said flexible protrusion in a manner that places said diaphragm adjacent to said outer ear member to allow stretching diaphragm movement toward the user's ear canal and into said hollow interior of said sleeve to provide pressure equalization in response to changes in liquid pressure, and further so that when said device is secured within a user's ear positioning of said diaphragm blocks entry of all contaminants into the ear canal while it stretches toward the ear canal in response to increasing liquid pressure and thereby protects the user's ear from barotraumas as the depth of the liquid medium around the user increases and decreases according to the user's vertical movement.

2. The ear prophylactic of claim 1 further comprising porous barrier means adapted for sealing against said outer ear member for protection of said diaphragm from contact with large objects and also for protection of said diaphragm from harm due to activities involving the potential for sudden impact to the user's ear.

3. The ear prophylactic of claim 1 further comprising airtight and water tight sealing means between said sleeve and the flexible protrusion.

4. The ear prophylactic of claim 1 further comprising sealing means and wherein said sealing means is selected from a group consisting of sealing means positioned between said sleeve and said flexible protrusion, and sealing means positioned between said outer ear member and the ear of a user.

5. The ear prophylactic of claim 1 further comprising lanyard means that is adapted for prompt removal of said outer ear member, said flexible protrusion, and said sleeve from an ear after use.

6. The ear prophylactic of claim 1 further comprising a protuberance depending from said outer ear member and lanyard means attached to said protuberance, with said protuberance and lanyard means in combination being adapted for prompt removal of said outer ear member, said flexible protrusion, and said sleeve from an ear after use to protect the ear from infection and barotraumas.

7. The ear prophylactic of claim 1 wherein said material from which said diaphragm is made is selected from a group consisting of rubber, latex, and closed cell neoprene.

8. The ear prophylactic of claim 1 wherein said materials from which said outer ear member and said flexible protrusion are made are selected from a group consisting of silicone and wax.

9. The ear prophylactic of claim 1 wherein said sleeve is made from a polypropylene material.

10. The ear prophylactic of claim 1 wherein said sleeve said outer ear member, and said protrusion are all made from the same material.

11. The ear prophylactic of claim 1 wherein said outer ear member and said flexible protrusion are made from two different materials.

12. The ear prophylactic of claim 1 further comprising a protuberance depending from said outer ear member and adapted for prompt removal of said outer car member, said flexible protrusion, and said sleeve from an ear after use to protect the ear from infection and barotraumas, said protuberance remotely positioned from said flexible protrusion.

13. A method for protecting an ear having an ear canal from the adverse effects of infection and barotraumas when in and around water and other liquid media at depths less than thirty-three feet as well as depths greater than thirty-three feet, said method comprising the steps of:

providing a tapering and centrally void outer ear member configured to fit watertight and airtight within an ear and a centrally void flexible protrusion depending from said outer ear member that is configured for extending into the ear canal of the ear;

also providing a non-collapsing, flexible sleeve having a hollow interior and opposing ends, a stretchable water-resistant and air-resistant diaphragm, and sealing means;

using said sealing means to cause said diaphragm to become extended across one of said opposing ends of said sleeve;

securing said outer ear member and said flexible protrusion within an ear so that said flexible protrusion extends into the ear canal; and concentrically positioning said sleeve within said centrally void outer ear member and said centrally void flexible protrusion so that when a person having one of said outer ear members, one of said sleeves, and one of said diaphragms in each said ear is intending to enter a liquid medium greater than thirty-three feet in depth, said sleeves are positioned within said flexible protrusions in a manner that places said diaphragms adjacent to said flexible protrusions to allow stretching diaphragm movement toward the user's ear canal to provide pressure equalization in response to changes in liquid pressure, and when the person is at liquid depths less than thirty-three feet, said sleeve is positioned in a manner that places said diaphragm adjacent to said outer ear member to allow stretching diaphragm movement toward the user's ear canal and into said hollow interior of said sleeve to provide pressure equalization in response to changes in liquid pressure, and further positioning of said diaphragm blocks entry of all contaminants into the ear canal while it stretches toward the ear canal in response to increasing liquid pressure and thereby protects the adjacent ear from barotraumas as the depth of the liquid medium around the person increases and decreases according to the person's vertical movement.

14. The method of claim 13 wherein the order of said steps of using and securing may be reversed.

15. The method of claim 13 wherein the steps of securing and concentrically positioning are reversed in order.

16. The method of claim 13 further comprising a step of providing removal means adapted for prompt removal of said outer ear member, said flexible protrusion, and said sleeve from and ear after use, and wherein said removal means is selected from a group consisting of protuberances and lanyards.

17. The method of claim 13 wherein said diaphragm is selected from a group consisting of rubber diaphragms, latex diaphragms, and closed cell neoprene diaphragms, wherein said outer ear member is selected from a group consisting of silicone outer ear members and wax outer ear members, wherein said protuberance is selected from a group consisting of silicone protuberances and wax protuberances, and wherein said sleeve is made from a polypropylene material.

18. The method of claim 13 further comprising the steps of providing porous barrier means and sealing said porous barrier means against said outer ear member so as to protect said diaphragm from contact with large objects.

19. The method of claim 13 further comprising the steps of providing scaling means and securing said sealing means between said sleeve and said flexible protrusion.

20. The method of claim 13 further comprising the steps of providing sealing means and securing said sealing means between said outer ear member and the ear of a user.

* * * * *